United States Patent [19]

Jikihara et al.

[11] Patent Number: 5,110,342
[45] Date of Patent: May 5, 1992

[54] INDAN-1,3-DIONE DERIVATIVE AND HERBICIDAL COMPOSITION CONTAINING THE SAME AS ACTIVE INGREDIENT

[75] Inventors: Tetsuo Jikihara, Komae; Toyohiko Shike, Yokohama; Manabu Katsurada, Machida; Hisao Watanabe, Yokohama; Osamu Ikeda, Machida, all of Japan

[73] Assignee: Mitsubishi Kasei Corporation, Tokyo, Japan

[21] Appl. No.: 755,826

[22] Filed: Sep. 6, 1991

Related U.S. Application Data

[62] Division of Ser. No. 523,748, May 15, 1990, Pat. No. 5,076,830.

[30] Foreign Application Priority Data

May 16, 1989 [JP] Japan .................................. 1-122624

[51] Int. Cl.⁵ .................... A01N 43/00; C07C 49/215
[52] U.S. Cl. ........................................... 71/88; 71/94; 71/103; 568/327; 546/129; 546/344
[58] Field of Search ................ 71/88, 94, 103; 546/129, 344; 568/327

[56] References Cited

U.S. PATENT DOCUMENTS

| | | | |
|---|---|---|---|
| 3,452,009 | 6/1969 | Wendler | 549/512 |
| 4,136,192 | 1/1979 | Buckle et al. | 514/457 |
| 4,569,945 | 2/1986 | Campbell et al. | 568/327 |
| 4,629,492 | 12/1986 | Pews | 71/88 |
| 4,758,262 | 7/1988 | Shapiro | 71/88 |
| 4,961,775 | 10/1990 | Takatsuto et al. | 71/88 |

FOREIGN PATENT DOCUMENTS

| | | |
|---|---|---|
| 245170 | 9/1962 | Australia . |
| 0190945 | 8/1986 | European Pat. Off. . |
| 2127982 | 12/1972 | Fed. Rep. of Germany . |
| 1049868 | 10/1983 | U.S.S.R. . |
| 1380089 | 8/1975 | United Kingdom . |
| 1597831 | 9/1981 | United Kingdom . |

OTHER PUBLICATIONS

Japanese Abstracts of Japan, vol. 5, No. 195, 1981.

*Primary Examiner*—C. Warren Ivy
*Assistant Examiner*—Amelia A. Owens
*Attorney, Agent, or Firm*—David G. Conlin; Peter F. Corless

[57] ABSTRACT

The present invention provides an indan-1,3-dione derivative represented by the following formula (I):

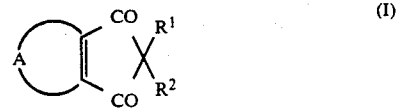

wherein $R^1$ represents a hydrogen atom or a lower alkyl group; $R^2$ represents a group represented by

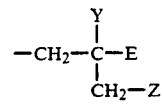

wherein E represents a (substituted) phenyl group or a (substituted) pyridyl group; Y represents a hydroxyl group; and Z represents a halogen atom, a (substituted) alkylsulfonyloxy group or a (substituted) phenylsulfonyloxy group, or Y and Z are bonded to represent —O—; and A represents a (substituted) 1,3-butadienylene group or a (substituted) 1,3-azabutadienylene group, and a herbicidal composition containing the same as an active ingredient.

7 Claims, No Drawings

INDAN-1,3-DIONE DERIVATIVE AND HERBICIDAL COMPOSITION CONTAINING THE SAME AS ACTIVE INGREDIENT

This is a divisional of copending application Ser. No. 07/523,748 filed on May 19, 1990, now U.S. Pat. No. 5,076,830.

BACKGROUND OF THE INVENTION

This invention relates to a novel indan-1,3-dione derivative and a herbicidal composition containing the same as an active ingredient.

Heretofore, various compounds having indan-1,3-dione structure have been known, and a known indan-1,3-dione derivative to be used in a specified field of art has a specific basic molecular structure depending on the field. Representative examples thereof may include a group of compounds known as a rodenticide and the structure has substantially been limited to 2-(aryl or aryl-substituted acyl)indan-1,3-dione derivatives.

On the other hand, as indan-1,3-dione derivatives having herbicidal activity, there has been known, for example, 1,3-dimethyl-4-(substituted benzoyl)-5-(indan-1,3-dion-2-yloxy)pyrazole (Japanese Patent Application Laid-Open (KOKAI) No. 56-118003 (1981)).

Heretofore, various compounds having herbicidal activities have been proposed, but not so many compounds having both safety to specific crops and satisfactory herbicidal activity have been developed. Also, considering with circumferential effect, it has been desired to develop chemicals capable of reducing an amount to be used.

SUMMARY OF THE INVENTION

The present invention relates to an indan-1,3-dione derivative represented by the following formula:

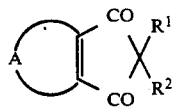
(I)

wherein $R^1$ represents a hydrogen atom or a lower alkyl group; $R^2$ represents a group represented by

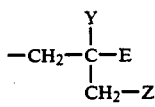

wherein E represents a phenyl group which may be substituted or a pyridyl group which may be substituted, Y represents hydroxyl group, and Z represents a halogen atom, an alkylsulfonyloxy group which may be substituted or a phenylsulfonyloxy group which may be substituted, or Y and Z are bonded to represent —O—; and A represents a 1,3-butadienylene group which may be substituted or a 1,3-azabutadienylene group which may be substituted, a herbicidal composition containing the same as an active ingredient, an indan-1,3-dione derivative represented by the following formula (II):

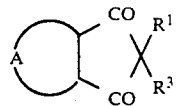
(II)

wherein $R^1$ represents a hydrogen atom or a lower alkyl group; $R^3$ represents a group represented by

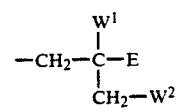

wherein E represents a phenyl group which may be substituted or a pyridyl group which may be substituted and $W^1$ and $W^2$ each represents hydroxyl group or $W^1$ forms a carbon-carbon bond with $W^2$; and A represents a 1,3-butadienylene group which may be substituted or a 1,3-azabutadienylene group which may be substituted, and a process for producing the derivatives of the formulae (I) and (II).

DETAILED DESCRIPTION OF THE INVENTION

The indan-1,3-dione derivatives to be used as the active ingredient of the herbicidal composition of the present invention can be shown by the above formula (I) and, in the following, representative examples of substituents in the formula (I) are shown.

$R^1$ is a hydrogen atom or a straight or branched $C_1$–$C_6$ alkyl group, and particularly preferably a straight or branched $C_1$–$C_6$ alkyl group.

$R^2$ is a group represented by

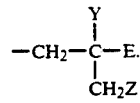

E represents a phenyl group or a pyridyl group each of which may be substituted by 1 to 3 substituents, and preferably a phenyl group or a pyridyl group which may be unsubstituted or substituted by 1 to 2 substituents. As a substituent for the phenyl group and the pyridyl group, there may be mentioned a halogen atom such as fluorine atom, chlorine atom, bromine atom and iodine atom; a $C_1$–$C_4$ alkyl group such as methyl group, ethyl group, n-propyl group and isopropyl group; a $C_1$–$C_3$ haloalkyl group which is substituted by 1 to 5 halogen atoms such as fluoromethyl group, chloromethyl group, bromomethyl group, difluoromethyl group, dichloromethyl group, trifluoromethyl group, trichloromethyl group, 1,1,2,2-tetrafluoroethyl group and pentafluoropropyl group; an $C_1$–$C_2$ alkoxy group which may be substituted by 1 to 5 halogen atoms such as methoxy group, ethoxy group, difluoromethoxy group, trifluoromethoxy group, 2,2,2-trifluoroethoxy group, 1,1,2,2-tetrafluoroethoxy group and 2-chloro-1,1,2-trifluoroethoxy group; nitro group; and cyano group, and preferably fluorine atom, chlorine atom, methyl group, trifluoromethyl group, methoxy group, nitro group and cyano group.

Y is a hydroxyl group and Z is a halogen atom such as fluorine atom, chlorine atom, bromine atom and iodine atom; a ($C_1$–$C_8$ alkyl) sulfonyloxy group which may be substituted; or a phenylsulfonyloxy group which may be substituted; and Z and Y may be combined with each other to represent —O—. Preferably, Z represents bromine atom, a (C$_1$-C$_6$ alkyl) sulfonyloxy group which may be substituted by 1 to 2 substituents, or a phenylsulfonyloxy group which may be substituted by 1 to 3 substituents, or it may be combined with Y to form —O—.

Examples of substituents for the alkylsulfonyloxy group are preferably a halogen atom such as fluorine atom, chlorine atom, bromine atom and iodine atom, and chlorine atom is particularly preferred. Also, examples of substituents for the phenylsulfonyloxy group may include a halogen atom such as fluorine atom, chlorine atom, bromine atom and iodine atom; and C$_1$-C$_3$ alkyl group which may be substituted by 1 to 5 halogen atoms such as methyl group, ethyl group, n-propyl group, trifluoromethyl group, trichloromethyl group, 1,1,2,2-tetrafluoroethyl group and pentafluoroethyl group; a C$_1$-C$_2$ alkoxy group which may be substituted by 1 to 5 halogen atoms such as methoxy group, ethoxy group, difluoromethoxy group, trifluoromethoxy group, 2,2,2-trifluoroethoxy group, 1,1,2,2-tetrafluoroethoxy group and 2-chloro-1,1,2-trifluoroethoxy group; nitro group or cyano group, and preferably fluorine atom, chlorine atom, methyl group, trifluoromethyl group, methoxy group, nitro group or cyano group, and two substituents adjacent to each other may be combined to form a fused ring.

In the formula (I), A represents a 1,3-butadienylene group which may be substituted by 1 to 4 substituents or a 1,3-azabutadienylene group which may be substituted by 1 to 3 substituents.

Examples of substituents for the 1,3-butadienylene group or the 1,3-azabutadienylene group may include a halogen atom such as fluorine atom, chlorine atom, bromine atom and iodine atom; a C$_1$-C$_3$ alkyl group which may be substituted by 1 to 5 halogen atoms such as methyl group, ethyl group, propyl group, chloromethyl group, dichloromethyl group, trifluoromethyl group, trichloromethyl group, 1,1,2,2-tetrafluoroethyl group and pentafluoropropyl group; a C$_1$-C$_2$ alkoxy group which may be substituted by 1 to 4 halogen atoms such as methoxy group, ethoxy group, difluoromethoxy group, trifluoromethoxy group, 2,2,2-trifluoroethoxy group, 1,1,2,2-tetrafluoroethoxy group and 2-chloro 1,1,2-trifluoroethoxy group; nitro group or cyano group, and preferably fluorine atom, chlorine atom or a C$_1$-C$_3$ alkyl group.

The compound represented by the following formula (II) is useful as an intermediate for synthesis of the compound represented by the formula (I).

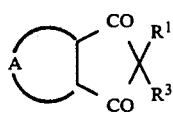
(II)

In the above formula, A and R$^1$ are the same as defined in the formula (I), and preferred substituents are also the same. R$^3$ is represented by

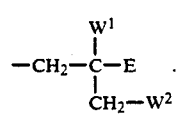

E is the same as defined in the formula (I), and preferred substituents are also the same as defined above. Also, in the groups, W$^1$ and W$^2$ each represents hydroxyl group or W$^1$ forms a carbon-carbon bond with W$^2$.

The compound represented by the above formula (II) can be synthesized, for example, according to the following reaction schemes (1) and (2).

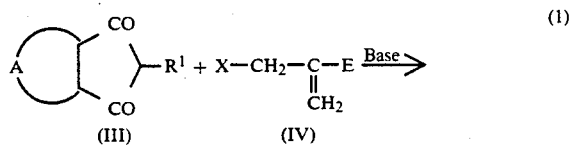
(1)

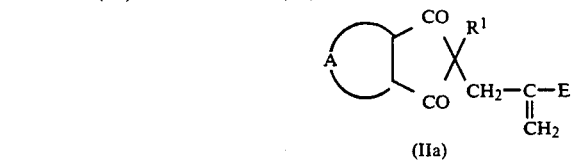
(IIa)

In the above reaction scheme, X represents a halogen atom, and other symbols have the same meanings as defined above.

The above reaction can be carried out in or without a solvent in the presence of a suitable base. Suitable solvents may include, for example, an aprotic solvent such as N,N-dimethylformamide, N-methylpyrrolidone, dimethyl sulfoxide, acetonitrile, tetrahydrofuran, dioxane and 1,2-dimethoxyethane; alcohols such as methanol, ethanol, 2-propanol and n-butanol; ketones such as acetone and methyl ethyl ketone; esters such as ethyl acetate; aromatic hydrocarbons such as benzene, toluene and xylene; and water. Examples of the base may include sodium hydride, potassium hydride, metal sodium, metal potassium, sodium hydroxide, potassium hydroxide, sodium carbonate and potassium carbonate.

The ratio of the compound (III) and the compound (IV) when effecting the reaction is usually 1:0.8 to 2 (molar ratio). The amount of the base is 1 to 3 mole based on one mole of the compound (III).

The reaction temperature is usually in the range of $-20°$ to 200° C., preferably $-5°$ to 120° C., and the reaction time is 0.5 to 48 hours, usually 1 to 12 hours.

The starting compound (III) can be prepared according to the method as described in, for example, C. F. Koelsch and D. J. Byers, J. Am. Chem. Soc., 62, 560 (1940), or W. A. Mosher and R. W. Soeder, J. Org. Chem., 36, 1561 (1971).

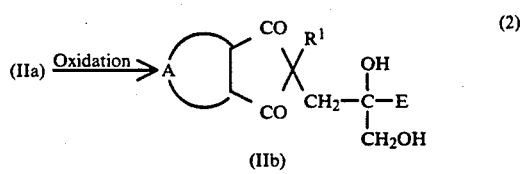
(2)

In the above reaction scheme, A, R$^1$ and E have the same meanings as defined above.

The above reaction is classified into an oxidation reaction of olefins to 1,2-diols in view of organic synthetic chemistry. There are many publications in which the above reaction is described, for example, in "Methods for the Oxidation of Organic Compounds" written by Alan H. Haines, pp. 73-93 (1985), ACADEMIC PRESS.

This reaction can be carried out, for example, by reacting a mixture of the compound (IIa), hydrogen peroxide and an aliphatic acid such as formic acid and acetic acid at usually 0° to 120° C., preferably 20° to 80° C. for 0.5 to 24 hours, preferably 1 to 12 hours in the presence or absence of a solvent, and then treating the reaction mixture with an aqueous solution or an alcoholic aqueous solution containing 5 to 50% by weight of a base such as triethylamine and sodium hydroxide at usually 0° to 100° C., preferably 20° to 80° C.

The ratio of the compound (IIa), hydrogen peroxide and the aliphatic acid is usually 1:1 to 3:1 to 20 in molar ratio and the solvent to be used may include water, dichloromethane, chloroform, benzene, toluene, methanol, ethanol, 2-propanol or a mixture thereof.

The compound represented by the formula (I) can be synthesized by using the above IIa or IIb, for example, according to the following reaction scheme.

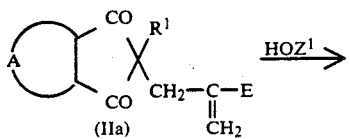  (3)

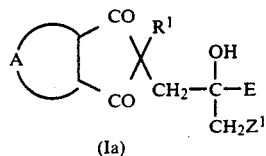
(Ia)

In the above reaction scheme, $Z^1$ represents a halogen atom and the other symbols have the same meanings as defined above.

The above reaction can be carried out in water or an aqueous solvent by reacting the compound (IIa) with a halogenating agent such as alkali metal salt of hypohalogenous acids, alkali metal salt of halogenous acids, N-halogenosuccimides, chlorine, bromide and iodine, in the presence or absence of aliphatic acids such as acetic acid or mineral acids such as hydrochloric acid and/or heavy metal compounds such as mercuric acetate and mercuric oxide. The halogenating agent is used in an amount of 1 to 5 mole in terms of halogen atom based on one mole of the compound of the formula IIa. The aqueous solvent to be used may include a mixture of water and tetrahydrofuran, dimethyl sulfoxide or dioxane. The reaction temperature is usually in the range of −30° to 100° C., preferably −10° to 60° C., and the reaction time is usually 0.1 to 24 hours, preferably 0.5 to 6 hours.

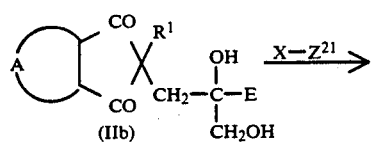  (4)

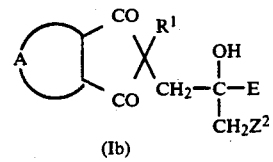
(Ib)

In the above reaction scheme, $Z^2$ represents an alkylsulfonyloxy group which may be substituted or a phenylsulfonyloxy group which may be substituted, $Z^{21}$ represents an alkylsulfonyl group which may be substituted or a phenylsulfonyl group which may be substituted, corresponding to $Z^2$, X represents a halogen atom or the same meaning as $Z^2$, and the other symbols have the same meanings as defined above.

The above sulfonylation reaction can be carried out in the presence or absence of a solvent and in the presence or absence of a base. When the solvent is used, suitable solvent may include N,N-dimethylformamide, N-methylpyrrolidone, tetrahydrofuran, dioxane, 1,2-dimethoxyethane, benzene, toluene, ethyl acetate, methylene chloride and chloroform. As the base, there may be mentioned pyridine, triethylamine, N,N-dimethylaniline, N,N-diethylaniline, sodium hydrogen carbonate, potassium hydrogen carbonate, sodium hydroxide, potassium hydroxide and sodium hydride. The sulfonylation agent is used in an amount of 1 to 2 mole, and the base is used in an amount of 1 mole to the same mole as the solvent used. Based on one mole of the compound of the formula IIb. The reaction temperature is usually in the range of −20° to 100° C., preferably 0° to 60° C., and the reaction time is usually 1 to 24 hours.

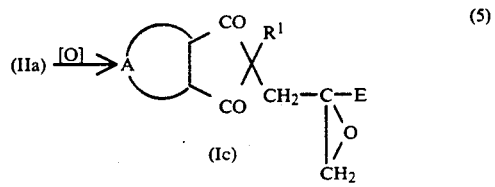  (5)

In the above reaction scheme, A, $R^1$ and E have the same meanings as defined above.

The above oxidation reaction is carried out in a solvent such as chloroform, methylene chloride, carbon tetrachloride, benzene, cyclohexane, n-hexane, methanol, ethanol, propanol, butanol, acetic acid and water, in the presence of an oxidizing agent such as peracids including m-chloroperbenzoic acid and peracetic acid, peroxides including hydrogen peroxide and t-butylhydroperoxide, and alkali metal salt of hypohalogenous acids. The oxidizing agent is used in an amount of 1 to 10 mole based on one mole of the compound of the formula IIa. The reaction temperature is usually in the range of −20° to 120° C., preferably 0° to 80° C., and the reaction time is usually 1 to 24 hours, preferably 1 to 12 hours.

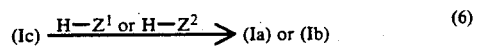  (6)

In the above reaction scheme, $Z^1$ and $Z^2$ have the same meanings as defined above.

The above reaction is carried out by reacting a hydrogen halide or a sulfonic acid in a solvent such as water, diethyl ether, diisopropyl ether, tetrahydrofuran, dioxane, benzene, toluene, methylene chloride, chloroform, carbon tetrachloride, N,N-dimethylformamide, N-methylpyrrolidone, ethyl acetate, 2-propanol, 2-methyl-2-propanol or a mixed solvent thereof in the presence or absence of an organic base such as pyridine, picoline and quinoline or an inorganic base such as sodium (potassium) hydroxide, sodium (potassium) carbonate and sodium (potassium) bicarbonate. The amount of the hydrogen halide or the sulfonic acid to be used is 1 to 10 mole and that of the base is 1 to 10 mole based on one mole of the compound of formula Ic. The reaction temperature is usually in the range of −120° to 150° C., preferably 60° to 80° C., and the reaction time is usually 0.1 to 48 hours, preferably 0.5 to 12 hours.

$$(Ia) \text{ or } (Ib) \xrightarrow{\text{Base}} (Ic) \quad (7)$$

The above reaction is carried out in a solvent such as methanol, ethanol, 2-propanol, acetone, methyl ethyl ketone, ether, tetrahydrofuran, dioxane, benzene, toluene, ethyl acetate, N,N-dimethylformamide, dimethyl sulfoxide, N-methylpyrrolidone, acetonitrile and water or a mixed solvent thereof in the presence of a base such as sodium hydrogen carbonate, potassium hydrogen carbonate, sodium carbonate, potassium carbonate, sodium hydroxide, potassium hydroxide, sodium hydride, sodium alcoholate, pyridine, triethylamine, N,N-dimethylaniline and N,N-diethylaniline at usually $-10°$ to $120°$ C., preferably $0°$ to $80°$ C.. The reaction time is usually 0.1 to 12 hours. The amount of the base to be used is 1 to 2 mole based on one mole of the compound of the formula Ia or Ib.

The thus obtained compound of the present invention has optical isomers and the compound is usually obtained as a racemate, and each enantiomer can be obtained by the known method such as asymmetric synthesis. The compound of the present invention can be used either racemate or each enantiomer alone as a herbicidally active ingredient.

The compound (I) of the present invention can be used alone as a herbicide or in the form of preparation such as wettable powder, granules, emulsifiable concentrate and flowable agent prepared according to the conventional method using suitable carriers or surfactants. Examples of the carrier and the surfactant may include those as described in, for example, Japanese Patent Application Laid-Open (KOKAI) No. 60-25986(1985). Further, the herbicidal composition containing the compound (I) of the present invention can be used in combination with other agricultural chemicals such as insecticide, fungicide, herbicide, growth regulator and fertilizer.

The amount of the herbicidal composition of the present invention to be used is different depending on the kinds of the compounds to be used, kinds of weeds to be treated, time of application, method of treatment or soil state, but usually it is suitable in the range of 0.25 to 40 grams, preferably 1 to 20 grams per one are as an active ingredient.

In the compounds of the present invention, there are some fluctuations in physiological activities depending on the kinds of functional groups and positions thereof, but any of the compound of the present invention shows extremely high herbicidal activity against *Echinochloa crusgalli* from pre-emergence to after grown up, which is the most harmful weeds against rice cultivation in paddy fields, and is extremely low in phytotoxicity to paddy rice.

Also, the compounds of the present invention have activities not only in paddy soil application but also in upland soil application, and have high herbicidal activity against annual weeds such as *Digitaria sanguinalis, Echinochloa crusgalli* and *Setaria viridis,* and extremely low phytotoxicity to crops such as soybean, cotton, corn, wheat, barley and beet.

The herbicidal activities of the compounds of the present invention is most remarkable to gramineous weeds such as *Digitaria sanguinalis, Echinochloa crusgalli* and *Setaria viridis,* and further remarkable to cyperaceous weeds such as *Cyperus microiria, Cyperus difformis, Scirpus juncoides* and *Eleocharis acicularis,* and annual broadleaved weeds such as *Chenopodium album L., Amaranthus retroflexus, Persicaria blumei* gross, *Rotala indica* and *Monochoria vaginalis.*

Also, the compounds of the present invention show somewhat low herbicidal activities to annual braodleaved weeds and perennial weeds which are grown up, but it can be possible to remarkably enlarge a herbicidal spectrum by using combinedly a herbicide effective to these weeds, and it is also possible to more stabilize the effect.

In this case, examples of herbicide suitably mixed are exemplified as shown below.

Pyrazole type herbicides: 4-(2,4-dichlorobenzoyl)-1,3-dimethylpyrazol-5-yl p-toluenesulfonate, 4-(2,4-dichlorobenzoyl)-1,3-dimethyl-5-phenacyloxypyrazole, 4-(2,4-dichloro-3-methylbenzoyl)-1,3-dimethyl-5-(4-methylphenacyloxy)pyrazole, 4-(2,4-dichlorobenzoyl-1-methyl-5-phenacyloxypyrazole, etc.;

Sulfonylurea type herbicides: methyl 2-(4,6-dimethoxypyrimidin-2-ylcarbamoylaminosulfonylmethyl)-benzoate, ethyl 5-(4,6-dimethoxypyrimidin-2-yl-carbamoylaminosulfonyl)-1-methylpyrazole-4-carboxylate, 2-chloro-N-(4-methoxy-6-methyl-1,3,5-triazin-2-ylaminocarbonyl)benzenesulfonamide, methyl 2-(4-methoxy-6-methyl-1,3,5-triazin-2-ylcarbamoylaminosulfonyl)-benzoate, methyl 2-(4,6-dimethylpyrimidin-2-ylcarbamoylaminosulfonyl)benzoate, ethyl 2-(4-chloro-6-methoxypyrimidin-2-ylcarbamoylaminosulfonyl)benzoate, etc.;

Phenoxy type herbicides: 2,4-dichlorophenoxyacetic acid and derivatives thereof, 4-chloro-2-methylphenoxyacetic acid and derivatives thereof, 4-(4-chloro-2-methylphenoxy)butyric acid and derivatives thereof, S-ethyl 4-chloro-2-methylphenoxythioacetate, 2-(2-naphthoxy)propionanilide, 2-(2,4-dichloro-3-methylphenoxy)propionanilide, butyl 2-[4-(5-trifluoromethyl-2-pyridyloxy)phenoxy]propionate, etc.;

Haloacetanilide type herbicides: 2-chloro-2',6'-diethyl-N-methoxymethylacetanilide, 2 chloro-2',6'-diethyl-N-butoxymethylacetanilide, 2-chloro-2'-ethyl-6'-methyl-N-(2-methoxy-1-methylethyl)acetanilide, 2-chloro-2',6'-diethyl-N-propoxyethylacetanilide, ethyl N-chloroacetyl-N-(2,6-diethylphenyl)aminoacetate, 2-chloro-2',6'-dimethyl-N-(3-methoxy-2-tenylmethyl)acetanilide, etc.;

Acid amide type herbicides: 3',4'-dichloropropionanilide, 2',3'-dichloro-4-ethoxymethoxybenzanilide, 2-bromo-3,3-dimethyl-N-(α,α-dimethylbenzyl)butyramide, 2-benzothiazol-2-yloxy-N-methylacetanilide, 2',4'-difluoro-2-(3-trifluoromethylphenoxy)nicotinanilide, 2,6-dimethoxy-N-[3-(1-ethyl-1-methylpropyl) isoxazol-5-yl]benzamide, etc.;

Carbamate type herbicides: S-(4-chlorobenzyl)-N,N-diethylthiolcarbamate, S-ethyl-N,N-hexamethylenethiolcarbamate, N,N-hexamethylene-S-isopropylthiolcarbamate, S-benzyl-N-ethyl-N-(1,2-dimethylpropyl)thiolcarbamate, S-(1-methyl-1-phenethyl) pyperidin-1-carbothioate, O-(3-t-butylphenyl)-N-(6-methoxypyridin-2-yl)-N-methylthiocarbamate, S-ethyl-N,N-di-n-propylthiolcarbamate, S-ethyl-N,N-diisobutylthiolcarbamate, isopropyl-N-(3-chlorophenyl)carbamate, 3-methoxycarbonylaminophenyl-N-(3-methylphenyl)carbamate, S-(2,3-dichloroallyl)-N,N-diisopropylthiolcarbamate, S-(2,3,3-trichloroallyl)-N,N-diisopropylthiolcarbamate, methyl-N-(4-aminobenzenesulfonyl)carbamate, etc.;

Urea type herbicides: 1-(α,α-dimethylbenzyl)-3-(4-methylphenyl)urea, 3-(benzothiazol-2-yl)-1,3-dimethylurea, 3-(3,4-dichlorophenyl)-1-methoxy-1-methylurea, 3-(3,4-dichlorophenyl)-1,1-dimethylurea, 3-[4-(4-methylphenethyloxy)phenyl]1-methoxy-1-methylurea, 3-(4-isopropylphenyl) 1,1-dimethylurea, 1-(2-substituted benzyl)-3-(α,α-dimethylbenzyl)urea, etc.;

Diphenyl ether type herbidices: 2,4,6-trichloro-4'-nitrodiphenyl ether, 2,4-dichloro-3'-methoxy-4'-nitrodiphenyl ether, methy 5-(2,4-dichlorophenoxy)-2-nitrobenzoate, 3-[5-(2 chloro-4-trifluoromethylphenoxy)-2-nitrophenoxy]tetrahydrofuran, 5-(2-chloro-4-trifluoromethylphenoxy)-2-nitrobenzoic acid and a salt thereof, 2-chloro-3'-ethoxy-4'-nitro-4-trifluoromethyl-diphenyl ether, 1-ethoxycarbonylethyl 5-(2-chloro-4-trifluoromethylphenoxy) 2-nitrobenzoate, 5-(2-chloro-4-trifluoromethylphenoxy)-N-methanesulfonyl-2-nitrobenzamide, methyl 5-(2-chloro-4-trifluoromethylphenoxy)-2-nitroacetophenoneoxime-O-acetate, 3-amino-2-chloro-4-nitrodiphenyl ether, etc.;

Triazine type herbicides: 2-chloro-4-ethylamino-6-isopropylamino-1,3,5-triazine, 2,4-bis(ethylamino)-6-methylthio-1,3,5-triazine, 2-ethylamino-4-(1,2-dimethylpropylamino)-6-methylthio-1,3,5-triazine, 2,4-bis(isopropylamino)-6-methylthio-1,3,5-triazine, 4-amino-6-t-butyl-3-methylthio-1,2,4-triazin-5(4H)-one, 4-amino-6-t-butyl-3-ethylthio-1,2,4-triazin-5(4H)-one, 2-chloro-4,6-bis(ethylamino)-1,3,5-triazine, 2-(2-chloro-4-ethylamino-1,3,5-triazin-6-ylamino)-2-methylpropionitrile, etc.;

Dinitroaniline type herbicides: 2,6-dinitro-N,N-dipropyl-4-trifluoromethylaniline, N-(1-ethylpropyl)-3,4-dimethyl-2,6-dinitroaniline, 3,5-dinitro-N,N-dipropylsulfanilamide, etc.;

Nitrile type herbicides: 4-hydroxy-3,5-diiodobenzonitrile, 3,5-dibromo-4-hydroxybenzonitrile, 2,6-dichlorobenzonitrile, etc.;

Phosphorus containing herbicides: O-ethyl-O-(5-methyl-2-nitrophenyl)-N-sec-butylphosphoramidate, S-(2-benzenesulfonylaminoethyl)-O-diisopropylphosphorodithioate, S-(2-methylpiperidin-1-yl)carbonylmethyl-O-dipropylphosphorodithioate, N-(phosphonomethyl)glycine, ammonium (3-amino-3-carboxy)-propylmethylphosphinate, sodium (2-amino 4-methylphosphino)butyrylalanylalaninate, etc.;

Quaternary ammonium salt type herbicides: 1,1'-ethylene-2,2'-bipyridylium dibromide, 1,1'-dimethyl-4,4'-bipyridylium dichloride, etc.;

Other herbicides: 3,6-dichloro-2-methoxybenzoic acid, 3,7-dichloroquinoline-8-carboxylic acid, pentachlorophenol, 2-sec-butyl-4,6-dinitrophenol, 2-amino-3-chloro-1,4-naphthoquinone, 1,2-dihydropyridazin-3,6-dione, 3-(2-methylphenoxy)pyridazine, 3-isopropyl-1H-2,1,3-benzothiadiazin-4(3H)-one-2,2-dioxide, 2,2-dichloropropionic acid, 2,2,3,3-tetrafluoropropionic acid, methyl 6-(4-isopropyl-4-methyl-5-oxo-2-imidazolin-2-yl) 3(4)-methylbenzoate, 2-(4-isopropyl-4-methyl-5-oxo-2-imidazolin-2-yl)nicotinic acid and a salt thereof, 2-(4-isopropyl-4-methyl-5-oxo 2-imidazolin-2-yl)quinoline-3-carboxylic acid, 5-ethyl-2-(4-isopropyl-4-methyl-5-oxo-2-imidazolin-2-yl)nicotinic acid, 1-methyl-4-(1-methylethyl)-2-(2-methylphenylmethoxy)-7-oxabicyclo-[2,2,1]heptane, 1-(3-methylphenyl)-5-phenyl-1H-1,2,4-triazol-3-carboxamide, 2-N-ethoxybutylimidoyl)-5-(2-ethylthiopropyl)-3-hydroxy-2-cyclohexen-1-one, 2-(3,5-dichlorophenyl)-2-(2,2,2-trichloroethyl)oxirane, N-[4-(4-chlorobenzyloxy)phenyl]-3,4,5,6-tetrahydrophthalimide, N-(4-chloro-2-fluoro-5-propargyloxyphenyl)-3,4,5,6-tetrahydrophthalimide, 3-(2,4-dichloro-5-isopropoxyphenyl)-5-t-butyl-1,3,4-oxadiazol-2(3H)-one, 4-methoxy-3,3'-dimethylbenzophenone, 2-ethoxy-2,3-dihydro-3,3-dimethyl-5-benzofuranylmethanesulfonate, 1-methyl-3-phenyl-5-(3-trifluoromethylphenyl)pyridin-4(1H)-one, 2-(2-chlorophenyl)methyl-4,4-dimethyl-3-isoxazolidinone, (E),(E)-2-[1-(3-chloropropen-2-yloxyimino)butyl]-5-(2-ethylthiopropyl)-3-hydroxy-2-cyclohexen-1-one, 2-(1-ethoxyiminopropyl)-3-hydroxy-5-mesityl-2-cyclohexen-1-one, etc.

These may be used in combination of two or more.

In the following, the present invention will be explained in more detail by referring to Examples, but the present invention is not limited by these Examples so long as they do not exceed the gist of the invention.

EXAMPLE 1

Preparation of 2-[2-(3-chlorophenyl)propen-3-yl]-2-methylindan-1,3-dione

In 10 ml of dried dimethyl cellosolve was dissolved 1.60 g of 2-methylindan-1,3-dione, and to the solution was added 0.48 g of 50% sodium hydride and the mixture was stirred at room temperature for 30 minutes. Then, 1.87 g of m-chloro-α-chloromethylstyrene was added to the mixture and the mixture was stirred under heating at 70° C. for 3 hours. Water was poured into the reaction mixture, and the reaction mixture was extracted with ethyl acetate. The organic layer was washed with water and with saturated saline solution, dried over anhydrous magnesium sulfate and the solvent was removed. The residue was separated and purified by silica gel column chromatography (developing solvent: n-hexane/ethyl acetate=6/1) to obtain 1.57 g of the compound No. 102 shown in Table 1.

$n_D^{25}$ 1.5968

$^1$H-NMR (CCl$_4$-TMS) δ: 1.32 (s, 3H), 3.07 (s, 2H), 5.03 (s, 2H), 6.90 (m, 4H), 7.77 (m, 4H)

EXAMPLE 2

Preparation of 5-chloro-2-[2-(6-chloro-2-pyridyl)-propen-3-yl]-2-methylindan-1,3-dion In 20 ml of methanol was dissolved 1.32 g of 85% potassium hydroxide, and then 3.89 g of 5-chloro-2-methylindan-1,3-dione, 3.76 g of 6-chloro-2-(1-chloromethylvinyl)pyridine and 0.05 g of potassium iodide were added to the solution. After refluxing under heating for 3 hours, the solvent was evaporated and water was poured. The reaction mixture was extracted with ethyl acetate, the organic layer was washed with water and with a saturated saline solution, and then dried over anhydrous magnesium sulfate. After the solvent was evaporated, the residue was separated and purified by silica gel column chromatography (developing solvent: n-hexane/ethyl acetate=5/1) to obtain 6.02 g of the compound No. 115 shown in Table 1.

m.p. 72° to 73° C.

$^1$H-NMR (CCl$_4$TMS) δ: 1.27 (s, 3H), 3.05 (s, 2H), 5.28, 5.65 (each s, 2H), 7.06, 7.17 (each d, 2H), 7.46 (t, 1H), 7.72 (s, 3H)

EXAMPLE 3

Preparation of 2-ethyl-2-(2,3-dihydroxy-2-phenylpropyl)-indan-1,3-dion

In 25 ml of dichloromethane were dissolved 25.6 g of 88% formic acid and 7.9 g of 30% hydrogen peroxide, and then 10.2 g of 2-ethyl-2-(2-phenylpropen-3-yl)indan-1,3-dione was added to the solution. After refluxing under heating for 10 hours, excess peroxide was decomposed with 10% sodium thiosulfate aqueous solution and the mixture was evaporated to dryness by azeotroping with toluene. Then, 30 ml of methanol, 20 ml of triethylamine and 20 ml of water were added thereto and the mixture was stirred at 50° C. for 5 hours. After condensing, the reaction mixture was poured into water and was extracted with ethyl acetate, and the organic layer was washed with water and then with a saturated saline solution, and dried over anhydrous magnesium sulfate. After the solvent was evaporated, n-hexane was added to the residue and precipitated crystals were collected by filtration. The resulting crystals were recrystallized from a small amount of methanol to obtain 9.43 g of the compound No. 127 shown in Table 1.

m.p. 138° to 139° C.

IR (KBr) cm$^{-1}$: 3380, 3326, 1719, 1694, 1603, 1246, 1225.

In the same manner as in the above examples, the compounds shown in Table 1 were prepared. In each case, the chemical structure was identified by IR spectrum and $^1$H-NMR.

TABLE 1

| Compound No. | A | $R^1$ | $R^3$ E | $W^1$ | $W^2$ | Physical property | Preparation method (Example No.) |
|---|---|---|---|---|---|---|---|
| 101 | —CH=CHCH=CH— | —CH$_3$ | phenyl | | Carbon-carbon bond | mp 89.5–90° C. | 1 |
| 102 | —CH=CHCH=CH— | —CH$_3$ | 2-Cl-phenyl | | Carbon-carbon bond | $n_D^{25}$ 1.5968 | 1 |
| 103 | —CH=CHCH=CH— | —CH$_3$ | 2-Cl-phenyl | —OH | —OH | mp 132.5–133.5° C. | 3 |
| 104 | —CH=CHCH=CH— | —CH$_3$ | 2-CF$_3$-phenyl | | Carbon-carbon bond | $n_D^{25}$ 1.5477 | 2 |
| 105 | —CH=CHCH=CH— | —CH$_3$ | 2-NO$_2$-phenyl | | Carbon-carbon bond | mp 81–82° C. | 2 |
| 106 | —CH=CHCH=CH— | —CH$_3$ | 2-Cl-3-F-phenyl | | Carbon-carbon bond | mp 56–57° C. | 2 |
| 107 | —CH=CHCH=CH— | —CH$_3$ | 2,4-Cl$_2$-phenyl | | Carbon-carbon bond | mp 63–65° C. | 2 |

TABLE 1-continued

| Compound No. | A | $R^1$ | $R^3$ E | $W^1$ | $W^2$ | Physical property | Preparation method (Example No.) |
|---|---|---|---|---|---|---|---|
| 108 | —CH=CHCH=CH— | —CH$_3$ | 2-chloropyridin-6-yl (Cl, N) | | | Carbon-carbon bond; mp 85.5–86° C. | 1 |
| 109 | —CH=CHCH=CH— | —CH$_3$ | 2-methoxypyridin-6-yl (OCH$_3$, N) | | | Carbon-carbon bond; mp 112–114° C. | 2 |
| 110 | —CH=CHCH=CH— | —CH$_3$ | 2,6-dichloropyridin-4-yl | | | Carbon-carbon bond; mp 117–118° C. | 2 |
| 111 | —CF=CHCH=CH— | —CH$_3$ | 3-chlorophenyl | | | Carbon-carbon bond; $n_D^{25}$ 1.5883 | 2 |
| 112 | —CF=CHCH=CH— | —CH$_3$ | 2-chloropyridin-6-yl | | | Carbon-carbon bond; mp 92–93° C. | 2 |
| 113 | —CH=CClCH=CH— | —CH$_3$ | phenyl | | | Carbon-carbon bond; $n_D^{25}$ 1.5931 | 2 |
| 114 | —CH=CClCH=CH— | —CH$_3$ | 3-chlorophenyl | | | Carbon-carbon bond; mp 53–54° C. | 2 |
| 115 | —CH=CClCH=CH— | —CH$_3$ | 2-chloropyridin-6-yl | | | Carbon-carbon bond; mp 72–73° C. | 2 |
| 116 | —CH=CClCH=CH— | —CH$_3$ | 2-methoxypyridin-6-yl | | | Carbon-carbon bond; $n_D^{25}$ 1.5899 | 2 |

TABLE 1-continued

Structure: A-ring fused to (CO-C(R¹)(CH₂-)-CO) with CH₂-C(E)(W¹)(CH₂-W²) side chain (R³ = E, W¹, W²)

| Compound No. | A | R¹ | R³ E | W¹ | W² | Physical property | Preparation method (Example No.) |
|---|---|---|---|---|---|---|---|
| 117 | —CH=CClCH=CH— | —CH₃ | 2,5-dichlorophenyl with =N— (CH=N, 2,5-Cl₂-C₆H₃) | | Carbon-carbon bond | mp 113–114° C. | 2 |
| 118 | —CH=C(CH₃)CH=CH— | —CH₃ | phenyl | | Carbon-carbon bond | $n_D^{25}$ 1.5812 | 2 |
| 119 | —CH=C(CH₃)CH=CH— | —CH₃ | 3-chlorophenyl | | Carbon-carbon bond | $n_D^{25}$ 1.5902 | 2 |
| 120 | —CH=C(CH₃)CH=CH— | —CH₃ | 3-chlorophenyl | —OH | —OH | Amorphous*¹ solid | 3 |
| 121 | —CH=C(CH₃)CH=CH— | —CH₃ | 2-chloropyridin-6-yl | | Carbon-carbon bond | $n_D^{25}$ 1.5948 | 2 |
| 122 | —CH=C(CH₃)CH=CH— | —CH₃ | 2-(trifluoromethyl)pyridin-6-yl | | Carbon-carbon bond | mp 55–56° C. | 2 |
| 123 | —CH=C(CH₃)CH=CH— | —CH₃ | 2,6-dichloropyridin-4-yl | | Carbon-carbon bond | mp 85.5–86.5 | 2 |
| 124 | —CH=C(CH₃)CH=CH— | —CH₃ | 2-chloro-6-methoxypyridin-4-yl | | Carbon-carbon bond | mp 94.5–95.5° C. | 2 |
| 125 | —CH=CHCH=N— | —CH₃ | 3-chlorophenyl | | Carbon-carbon bond | mp 103–104° C. | 2 |

TABLE 1-continued

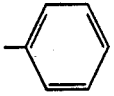

| Compound No. | A | R¹ | R³ E | W¹ | W² | Physical property | Preparation method (Example No.) |
|---|---|---|---|---|---|---|---|
| 126 | —CH=CHCH=CH— | —$C_2H_5$ | phenyl | | | Carbon-carbon bond<br>mp 79–80.5° C. | 2 |
| 127 | —CH=CHCH=CH— | —$C_2H_5$ | phenyl | —OH | —OH | mp 138–139° C. | 3 |
| 128 | —CH=CHCH=CH— | —$C_2H_5$ | 3-Cl-phenyl | | | Carbon-carbon bond<br>mp 52.5–53.5° C. | 2 |
| 129 | —CH=CHCH=CH— | —$C_2H_5$ | 3-Cl-phenyl | —OH | —OH | mp 125–126° C. | 3 |
| 130 | —CH=CHCH=CH— | —$C_2H_5$ | 3,5-diCl-phenyl | | | Carbon-carbon bond<br>mp 73–74° C. | 2 |
| 131 | —CH=CHCH=CH— | —$C_2H_5$ | 6-Cl-pyridin-2-yl | | | Carbon-carbon bond<br>mp 68–70° C. | 2 |
| 132 | —C($CH_3$)=CHCH=CH— | —$C_2H_5$ | 3-Cl-phenyl | | | Carbon-carbon bond<br>mp 54–56° C. | 2 |
| 133 | —CH=CHCH=CH— | n-$C_3H_7$ | 3-Cl-phenyl | | | Carbon-carbon bond<br>mp 47.5–49° C. | 2 |
| 134 | —CH=CHCH=CH— | n-$C_3H_7$ | 3-Cl-phenyl | —OH | —OH | mp 122–123° C. | 3 |

*¹IR spectrum of Compound No. 120
(KBr)cm⁻¹: 3396, 1702, 1607, 1283, 1250

EXAMPLE 4

Preparation of
2-[2-(3-chlorophenyl)-2,3-epoxypropyl]-2-ethylindan-1,3-dione

To the mixture of 1.62 g of 2-[2-(3-chlorophenyl)propen-3-yl]-2-ethylindan-1,3-dione, 0.34 g of sodium acetate trihydrate and 10 ml of chloroform was added 2.85 g of 40% peracetic acid.

After refluxing for 3 hours, excess peroxide was decomposed with 10% sodium thiosulfate aqueous solution, and the organic layer was washed with water, neutralized with a saturated sodium bicarbonate aqueous solution, washed with water and with a saturated saline solution, and dried over anhydrous magnesium sulfate. After the solvent was evaporated, the residue was separated and purified by silica gel column chromatography (developing solvent: n-hexane/ethyl acetate=4/1) to obtain 1.27 g of the compound No. 53 shown in Table 2.

m.p. 56.5° to 57.5° C.

$1_H$-NMR(CCl$_4$-TMS) δ: 0.67 (t, 3H), 1.83 (q, 2H), 2.67 (ABq, 2H), 2.71 (ABq, 2H), 6.85-7.30 (m, 4H), 7.60-8.15 (m, 4H).

EXAMPLE 5

Preparation of
2-(3-bromo-2-hydroxy-2-phenylpropyl)-2-ethylindan-1,3-dione

To the mixture of 1.53 g of 2-(2,3-epoxy-2-phenylpropyl)-2-ethylindan-1,3-dione, 15 ml of chloroform and 1 ml of dimethylformamide, was added 0.96 g of pyridine hydrobromide. After refluxing under heating for 6 hours, the reaction mixture was poured into water and was added 20 ml of chloroform.

The organic layer was washed with water and with a saturated saline solution, and dried over anhydrous magnesium sulfate. After evaporating the solvent, the residue was separated and purified by silica gel column chromatography (developing solvent: n-hexane/ethyl acetate=4/1) to obtain 0.45 g of the compound No. 36 shown in Table 2.

m.p. 89° to 92° C.

$1_H$-NMR(CDCl$_3$-TMS) δ: 0.50-1.00 (m, 3H), 1.50-2.20 (m, 2H), 2.50-3.80 (m, 5H), 6.80-8.10 (m, 9H).

EXAMPLE 6

Preparation of
2-[3-bromo-2-(3-chlorophenyl)-2-hydroxypropyl]-2,5-dimethylindan-1,3-dione In 30 ml of tetrahydrofuran was dissolved 1.98 g of 2-[2-(3-chlorophenyl)propen-3-yl]-2,5-dimethylindan-1,3-dione and then 10.86 g of N-bromosuccinimide and 15 ml of water were added to the solution, and the mixture was stirred at room temperature for 2 days. The liberated bromine was removed by sodium thiosulfate pentahydrate and tetrahydrofuran was distilled off. The residue mixture was extracted with ethyl acetate, and the organic layer was washed with water and with a saturated saline solution, then dried over anhydrous magnesium sulfate. After evaporation, the residue was separated and purified by silica gel column chromatography (developing solvent: n-hexane/ethyl acetate=3/1) to obtain 0.93 g of the compound No. 20 shown in Table 2.

m.p. 144° to 145° C.

IR (KBr) cm$^{-1}$: 3310, 2970, 1700, 1690, 1605, 1570, 1460.

EXAMPLE 7

Preparation of
2-[3-(3-chloro-n-propylsulfonyloxy)-2-hydroxy-2-phenylpropyl]-2-ethylindan-1,3-dione In 3.5 ml of pyridine was dissolved 0.81 g of 2-ethyl-2-(2,3-dihydroxy-2-phenylpropyl)indan-1,3-dione and then was added 0.62 g of 3-chloro-n-propylsulfonyl chloride. After was allowed to stand at 5° C. overnight, the reaction mixture was poured into 3N hydrochloric acid and extracted with ethyl acetate, and the organic layer was washed with water and with a saturated saline solution, and dried over anhydrous magnesium sulfate. After evaporation, the residue was separated and purified by silica gel column chromatography (developing solvent: chloroform/ethyl acetate=50/1) to obtain 0.94 g of the compound No. 42 shown in Table 2.

$1_H$-NMR(CDCl$_3$-TMS) δ: 0.83 (m, 3H), 1.50-3.70 (m, 1H), 3.80-4.40 (m, 2H), 6.80-8.10 (m, 9H).

IR (KBr) cm$^{-1}$: 3452, 2972, 1717, 1602, 1346, 1166.

In the same manner as mentioned above, other compounds shown in Table 2 were prepared according to the method described in the column of Example No. In each case, the chemical structure was identified by IR spectrum and $^1$H-NMR spectrum.

TABLE 2

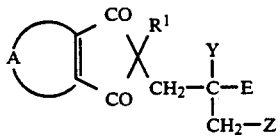

| Compound No. | A | R$^1$ | E | R$^2$ Y | Z | Physical property | Preparation method (Example No.) |
|---|---|---|---|---|---|---|---|
| 1 | —CH=CHCH=CH— | —CH$_3$ | | 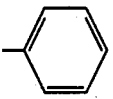 | —O— | mp 89.5-90° C. | 4 |

TABLE 2-continued

[Structure: A-ring with CO-CO group attached to C(R¹)(CH₂-)- group, connected to C(Y)(E)(CH₂Z)]

| Compound No. | A | R¹ | R² E | R² Y | R² Z | Physical property | Preparation method (Example No.) |
|---|---|---|---|---|---|---|---|
| 2 | —CH=CHCH=CH— | —CH₃ | 3-Cl-C₆H₄ | —OH | —OSO₂CH₃ | Amorphous solid*2 | 7 |
| 3 | —CH=CHCH=CH— | —CH₃ | 3-Cl-C₆H₄ | —OH | —OSO₂-C₆H₄-4-CH₃ | Amorphous solid*2 | 7 |
| 4 | —CH=CHCH=CH— | —CH₃ | 3-Cl-C₆H₄ | —OH | —OSO₂-C₆H₄-4-OCH₃ | Amorphous solid*2 | 7 |
| 5 | —CH=CHCH=CH— | —CH₃ | 3-Cl-C₆H₄ | —OH | —OSO₂-(2-F,4-Cl-C₆H₃) | Amorphous solid*2 | 7 |
| 6 | —CH=CHCH=CH— | —CH₃ | 3-Cl-C₆H₄ | —O— | | mp 62–66° C. | 4 |
| 7 | —CH=CHCH=CH— | —CH₃ | 3-CF₃-C₆H₄ | —O— | | $n_D^{25}$ 1.5392 | 4 |
| 8 | —CH=CHCH=CH— | —CH₃ | 3-NO₂-C₆H₄ | —O— | | mp 108.5–109.5° C. | 4 |
| 9 | —CH=CHCH=CH— | —CH₃ | 3-Cl,4-F-C₆H₃ | —O— | | mp 52–53° C. | 4 |
| 10 | —CH=CHCH=CH— | —CH₃ | 3,5-Cl₂-C₆H₃ | —O— | | mp 80–81° C. | 4 |

TABLE 2-continued

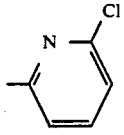

| Compound No. | A | R[1] | R[2] E | Y | Z | Physical property | Preparation method (Example No.) |
|---|---|---|---|---|---|---|---|
| 11 | —CH=CHCH=CH— | —CH₃ | 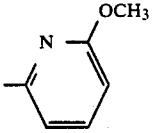 2-Cl pyridyl | | —O— | mp 127–127.5° C. | 4 |
| 12 | —CH=CHCH=CH— | —CH₃ | 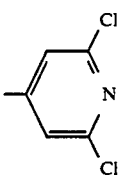 2-OCH₃ pyridyl | | —O— | mp 133–134° C. | 4 |
| 13 | —CH=CHCH=CH— | —CH₃ | 2,6-diCl pyridyl | | —O— | mp 134.5–135.5° C. | 4 |
| 14 | —CF=CHCH=CH— | —CH₃ | 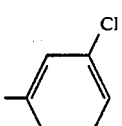 3-Cl phenyl | | —O— | mp 82–84° C. | 4 |
| 15 | —CF=CHCH=CH— | —CH₃ | 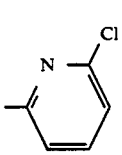 2-Cl pyridyl | | —O— | mp 90.5–93° C. | 4 |
| 16 | —CH=CClCH=CH— | —CH₃ | 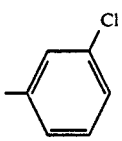 3-Cl phenyl | | —O— | mp 68–70° C. | 4 |
| 17 | —CH=CClCH=CH— | —CH₃ | 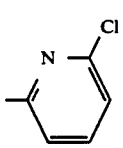 2-Cl pyridyl | | —O— | mp 92.5–93.5° C. | 4 |
| 18 | —CH=CClCH=CH— | —CH₃ | 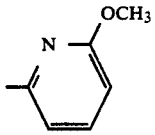 2-OCH₃ pyridyl | | —O— | mp 119–121° C. | 4 |
| 19 | —CH=CClCH=CH— | —CH₃ | 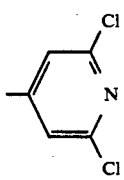 2,6-diCl pyridyl | | —O— | Amorphous solid*2 | 4 |

TABLE 2-continued

[Structure: A ring fused with CO-CO group attached to C(R¹)(CH₂-)— with CH₂-C(Y)(E)-CH₂-Z]

| Compound No. | A | R¹ | R² E | R² Y | R² Z | Physical property | Preparation method (Example No.) |
|---|---|---|---|---|---|---|---|
| 20 | —CH=C(CH₃)CH=CH— | —CH₃ | 3-Cl-phenyl | —OH | —Br | mp 144–145° C. | 6 |
| 21 | —CH=C(CH₃)CH=CH— | —CH₃ | 3-Cl-phenyl | —OH | —OSO₂CH₃ | Amorphous solid | 7 |
| 22 | —CH=C(CH₃)CH=CH— | —CH₃ | 3-Cl-phenyl | —OH | —OSO₂C₂H₅ | Amorphous solid | 7 |
| 23 | —CH=C(CH₃)CH=CH— | —CH₃ | 3-Cl-phenyl | —OH | —OSO₂C₄H₉-i | Amorphous solid | 7 |
| 24 | —CH=C(CH₃)CH=CH— | —CH₃ | 3-Cl-phenyl | —OH | —OSO₂CH₂Cl | Amorphous solid*2 | 7 |
| 25 | —CH=C(CH₃)CH=CH— | —CH₃ | 3-Cl-phenyl | —OH | —OSO₂-phenyl | Amorphous solid*2 | 7 |
| 26 | —CH=C(CH₃)CH=CH— | —CH₃ | 3-Cl-phenyl | —OH | —OSO₂-(4-CH₃-phenyl) | Amorphous solid*2 | 7 |
| 27 | —CH=C(CH₃)CH=CH— | —CH₃ | 3-Cl-phenyl | —OH | —OSO₂-(2-CN-phenyl) | Amorphous solid*2 | 7 |
| 28 | —CH=C(CH₃)CH=CH— | —CH₃ | 3-Cl-phenyl | —OH | —OSO₂-(3-CF₃-phenyl) | Amorphous solid*2 | 7 |

TABLE 2-continued

Structure: A ring fused with two CO groups connected to C(R¹)(—CH₂—C(E)(Y)(CH₂Z)) substituent (R²=C(E)(Y)(CH₂Z))

| Compound No. | A | R¹ | R² E | R² Y | R² Z | Physical property | Preparation method (Example No.) |
|---|---|---|---|---|---|---|---|
| 29 | —CH=C(CH₃)CH=CH— | —CH₃ | 3-Cl-C₆H₄— | —OH | —OSO₂-(3-CH₃-4-Cl-C₆H₃) | Amorphous solid*2 | 7 |
| 30 | —CH=C(CH₃)CH=CH— | —CH₃ | 3-Cl-C₆H₄— | —OH | —OSO₂-(5,6,7,8-tetrahydronaphth-2-yl) | Amorphous solid*2 | 7 |
| 31 | —CH=C(CH₃)CH=CH— | —CH₃ | 3-Cl-C₆H₄— | —O— | | mp 75–77° C. | 4 |
| 32 | —CH=C(CH₃)CH=CH— | —CH₃ | 2-Cl-pyridin-6-yl | —O— | | mp 76–78° C. | 4 |
| 33 | —CH=C(CH₃)CH=CH— | —CH₃ | 2-CF₃-pyridin-6-yl | —O— | | mp 80–81° C. | 4 |
| 34 | —CH=C(CH₃)CH=CH— | —CH₃ | 2,6-diCl-pyridin-4-yl | —O— | | Amorphous solid*2 | 4 |
| 35 | —CH=CHCH=N— | —CH₃ | 3-Cl-C₆H₄— | —O— | | n_D²⁵ 1.5798 | 4 |
| 36 | —CH=CHCH=CH— | —C₂H₅ | C₆H₅— | —OH | —Br | mp 89–92° C. | 5 |
| 37 | —CH=CHCH=CH— | —C₂H₅ | C₆H₅— | —OH | —OSO₂CH₃ | Amorphous solid*2 | 7 |
| 38 | —CH=CHCH=CH— | —C₂H₅ | C₆H₅— | —OH | —OSO₂C₂H₅ | Amorphous solid*2 | 7 |

TABLE 2-continued

[Structure: A-ring fused to two CO groups connecting to C(R¹)(CH₂-)(CH₂-C(Y)(E)(CH₂-Z))]

| Compound No. | A | R¹ | R² E | R² Y | R² Z | Physical property | Preparation method (Example No.) |
|---|---|---|---|---|---|---|---|
| 39 | —CH=CHCH=CH— | —C₂H₅ | phenyl | —OH | —OSO₂C₃H₇-n | Amorphous solid*2 | 7 |
| 40 | —CH=CHCH=CH— | —C₂H₅ | phenyl | —OH | —OSO₂C₄H₉-i | Amorphous solid*2 | 7 |
| 41 | —CH=CHCH=CH— | —C₂H₅ | phenyl | —OH | —OSO₂CH₂Cl | Amorphous solid*2 | 7 |
| 42 | —CH=CHCH=CH— | —C₂H₅ | phenyl | —OH | —OSO₂(CH₂)₃Cl | Viscous liquid*2 | 7 |
| 43 | —CH=CHCH=CH— | —C₂H₅ | phenyl | —OH | —OSO₂CH₂-phenyl | Amorphous solid*2 | 7 |
| 44 | —CH=CHCH=CH— | —C₂H₅ | phenyl | —O— | | mp 68–69° C. | 4 |
| 45 | —CH=CHCH=CH— | —C₂H₅ | 2-Cl-phenyl | —OH | —Br | mp 103–105° C. | 5 |
| 46 | —CH=CHCH=CH— | —C₂H₅ | 2-Cl-phenyl | —OH | —OSO₂CH₃ | mp 101–104° C. | 7 |
| 47 | —CH=CHCH=CH— | —C₂H₅ | 2-Cl-phenyl | —OH | —OSO₂C₂H₅ | Amorphous solid*2 | 7 |
| 48 | —CH=CHCH=CH— | —C₂H₅ | 2-Cl-phenyl | —OH | —OSO₂C₃H₇-n | Amorphous solid*2 | 7 |

TABLE 2-continued

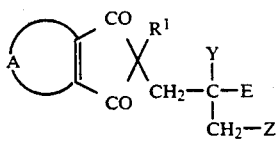

| Compound No. | A | R¹ | R² E | R² Y | R² Z | Physical property | Preparation method (Example No.) |
|---|---|---|---|---|---|---|---|
| 49 | $-CH=CHCH=CH-$ | $-C_2H_5$ | 3-Cl-phenyl | $-OH$ | $-OSO_2C_4H_9$-i | Viscous liquid*2 | 7 |
| 50 | $-CH=CHCH=CH-$ | $-C_2H_5$ | 3-Cl-phenyl | $-OH$ | $-OSO_2CH_2Cl$ | Viscous liquid*2 | 7 |
| 51 | $-CH=CHCH=CH-$ | $-C_2H_5$ | 3-Cl-phenyl | $-OH$ | $-OSO_2(CH_2)_3Cl$ | Viscous liquid*2 | 7 |
| 52 | $-CH=CHCH=CH-$ | $-C_2H_5$ | 3-Cl-phenyl | $-OH$ | $-OSO_2CH_2$-phenyl | Amorphous solid*2 | 7 |
| 53 | $-CH=CHCH=CH-$ | $-C_2H_5$ | 3-Cl-phenyl | | $-O-$ | mp 56.5–57.5° C. | 4 |
| 54 | $-CH=CHCH=CH-$ | $-C_2H_5$ | 3,5-diCl-phenyl | | $-O-$ | mp 116–117° C. | 4 |
| 55 | $-CH=CHCH=CH-$ | $-C_2H_5$ | 2-Cl-pyridin-6-yl | | $-O-$ | mp 95–96.5° C. | 4 |
| 56 | $-C(CH_3)=CHCH=CH-$ | $-C_2H_5$ | 3-Cl-phenyl | | $-O-$ | $n_D^{25}$ 1.5759 | 4 |
| 57 | $-CH=CHCH=CH-$ | $-n$-$C_3H_7$ | 3-Cl-phenyl | $-OH$ | $-OSO_2CH_3$ | Amorphous solid*2 | 7 |

TABLE 2-continued

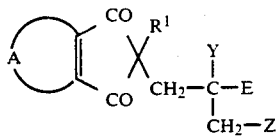

| Compound No. | A | R[1] | R[2] | | | Physical property | Preparation method (Example No.) |
|---|---|---|---|---|---|---|---|
| | | | E | Y | Z | | |
| 58 | —CH=CHCH=CH— | -n-C$_3$H$_7$ | (3-Cl-phenyl) | —OH | —OSO$_2$CH$_2$Cl | Viscous liquid*2 | 7 |
| 59 | —CH=CHCH=CH— | -n-C$_3$H$_7$ | (3-Cl-phenyl) | —O— | | $n_D^{25}$ 1.5780 | 4 |

*2; IR or NHR spectrum data are shown below.

| No. | IR or NMR spectrum |
|---|---|
| 2 | IR(KBr)cm$^{-1}$: 3420, 1718, 1600, 1335, 1178 |
| 3 | IR(KBr)cm$^{-1}$: 3335, 1700, 1600, 1360, 1178 |
| 4 | IR(KBr)cm$^{-1}$: 3320, 1706, 1595, 1360, 1169 |
| 5 | IR(KBr)cm$^{-1}$: 3338, 1700, 1595, 1362, 1182 |
| 19 | $^1$H-NMR(CDCl$_3$-TMS)$^\delta$: 1.25(s,3H) 2.67(ABq,2H) 2.65-2.80(m,2H) 7.01(s,2H) 7.60-8.20(m,3H) |
| 21 | IR(KBr)cm$^{-1}$: 3444, 1707, 1607, 1352, 1173 |
| 22 | IR(KBr)cm$^{-1}$: 3444, 1706, 1607, 1350, 1164 |
| 23 | IR(KBr)cm$^{-1}$: 3448, 1709, 1607, 1355, 1161 |
| 24 | IR(KBr)cm$^{-1}$: 3400, 1703, 1606, 1360, 1176 |
| 25 | IR(KBr)cm$^{-1}$: 3400, 1704, 1606, 1360, 1176 |
| 26 | IR(KBr)cm$^{-1}$: 3440, 1703, 1605, 1360, 1178 |
| 27 | IR(KBr)cm$^{-1}$: 3436, 2236, 1707, 1606, 1449, 1188 |
| 28 | IR(KBr)cm$^{-1}$: 3436, 1704, 1608, 1366, 1182 |
| 29 | IR(KBr)cm$^{-1}$: 3400, 1704, 1606, 1359, 1177 |
| 30 | IR(KBr)cm$^{-1}$: 3440, 1704, 1605, 1355, 1168 |
| 34 | $^1$H-NMR (CDCl$_3$-TMS)$^\delta$: 1.25(s,3H) 2.67 (ABq,2H) 2.58(s,3H) 2.68(d,2H) 6.97(s,2H) 7.55-8.00(m,3H) |
| 37 | IR(KBr)cm$^{-1}$: 3434, 1719, 1604, 1336, 1176 |
| 38 | IR(KBr)cm$^{-1}$: 3428, 1719, 1604, 1330, 1170 |
| 39 | IR(KBr)cm$^{-1}$: 3446, 1719, 1604, 1355, 1167 |
| 40 | IR(KBr)cm$^{-1}$: 3446, 1719, 1604, 1355, 1170 |
| 41 | IR(KBr)cm$^{-1}$: 3440, 1714, 1605, 1360, 1175 |
| 42 | IR(Liquid Film)cm$^{-1}$: 3452, 1717, 1602, 1346, 1166 |
| 43 | IR(KBr)cm$^{-1}$: 3442, 1708, 1602, 1354, 1170 |
| 47 | IR(KBr)cm$^{-1}$: 3446, 1707, 1602, 1349, 1165 |
| 48 | IR(KBr)cm$^{-1}$: 3446, 1707, 1600, 1350, 1160 |
| 49 | IR(KBr)cm$^{-1}$: 3442, 1716, 1705, 1602, 1354, 1161 |
| 50 | IR(KBr)cm$^{-1}$: 3436, 1705, 1603, 1368, 1178 |
| 51 | IR(KBr)cm$^{-1}$: 3446, 1716, 1705, 1602, 1345, 1167 |
| 52 | IR(KBr)cm$^{-1}$: 3436, 1706, 1602, 1355, 1173 |
| 57 | IR(Liquid Film)cm$^{-1}$: 3448, 1705, 1603, 1334, 1174 |
| 58 | IR(Liquid Film)cm$^{-1}$: 3446, 1701, 1602, 1362, 1178 |

Next, formulation examples of the compounds of the present invention are shown. In the following, "part" and "%" means "part by weight" and "% by weight", respectively.

FORMULATION EXAMPLE 1

Wettable Powder 40 parts of each compound of the present invention shown in Table 2, 20 parts of Carplex #80 (produced by Shionogi Seiyaku Co., trademark), 35 parts of N,N Kaolin clay (produced by Tsuchiya Kaolin Co., trademark) and 5 parts of higher alcohol sulfate type surfactant Sorpol 8070 (produced by Toho Kagaku Co., trademark) were uniformly mixed and pulverized to obtain a wettable powder containing 40% of an effective ingredient.

FORMULATION EXAMPLE 2

Granules 1 part of each compound of the present invention shown in Table 2, 45 parts of clay (produced by Nippon Talc Co.), 52 parts of bentonite (produced by Hojun Yoko Co.) and 2 parts of succinate type surfactant Aerol CT-1 (produced by Toho Kagaku Co., trademark) were mixed and pulverized, and then 20 parts of water was added to the mixture to effect kneading. Further, the mixed material was extruded from a nozzle having a diameter of 0.6 mm by using a pelletizer, and after drying at 60° C. for 2 hours, cut to a length of 1 to 2 mm to obtain granules containing 1% of an effective ingredient.

FORMULATION EXAMPLE 3

Emulsifiable Concentrate

In a mixed solvent composed of 30 parts of xylene and 25 parts of dimethylformamide was dissolved 30 parts of each compound of the present invention shown in Table 2, and then 15 parts of polyoxyethylene type surfactant Sorpol 3005X (produced by Toho Kagaku Co., trademark) was added to the solution to obtain an emulsifiable concentrate containing 30% of an effective ingredient.

FORMULATION EXAMPLE 4

Flowable Agent 30 parts of each compound of the present invention shown in Table 2 was mixed and dispersed well in a previously mixed solvent composed of 8 parts of ethylene glycol, 5 parts of Sorpol AC 3032 (produced by Toho Kagaku Co., trademark), 0.1 part of xanthan gum and 56.9 parts of water. Then, the slurry mixture was wet pulverized with Dyno-Mill (produced by Simmal Enterprizes Co.) to obtain a stable flowable agent containing 30% of effective ingredient.

TEST EXAMPLE 1

Paddy Soil Treatment Test

Resin pots, each having an area of 1/5000 are, were packed with alluvial clay loam at paddy field and after fertilization, a suitable amount of water was added and the soil was puddled. Then, the seeds of *Echinochloa crusgalli*, *Monochoria vaginalis* or *Scirpus juncoides* were sown uniformly within the soil surface of 1 cm. Then, the pots were filled with water to a depth of 3.5 cm from the soil surface.

Then, 3 days after from sowing, each granule containing the compound of the present invention shown in Table 2 or 2-methyl-1,3-indandione (hereinafter abbreviated to as the known compound A) as the active ingredient, which was obtained in the same manner as in Formulation example 2, were sprinkled on the surface of filled water in an application amount of 10 g per one are based on the active ingredient.

After treatment, leakage of water was effected for 2 days with 3 cm/day, and after 28 days, herbicidal effects were investigated and the results are shown in Table 3.

Evaluation of the herbicidal effects were obtained from $$\left(1 - \frac{\text{Fresh weight at above-ground part of weeds at treated district}}{\text{Fresh weight at above-ground portion of weeds at non-treated district}}\right) \times 100 = Y(\%)$$

and shown by the herbicidal effect coefficients with the following standard.

| Herbicidal effect coefficient | Y (%) |
|---|---|
| 0 | 0 to 4 |
| 1 | 5 to 29 |
| 2 | 30 to 49 |
| 3 | 50 to 69 |
| 4 | 70 to 89 |
| 5 | 90 to 100 |

TEST EXAMPLE 2

Upland Soil Treatment Test

Resin pots, each having an area of 1/5000 are, were packed with alluvial clay loam of volcanic ash and after fertilization, the seeds of *Echinochloa crusgalli*, *Digitaria sanguinalis* or *Setaria viridis* were sown uniformly within the soil surface of 1 cm.

On the next day of sowing, each wettable powder containing the compound of the present invention shown in Table 2 or the known compound A as the active ingredient, which was obtained in the same manner as in Formulation example 1, was sprayed after diluted with a predetermined amount of water in an application amount of 10 g per one are based on the active ingredient.

After 28 days from the treatment, herbicidal effects were investigated and the results are shown in Table 4. Evaluation of the herbicidal effects was represented by the same standard as in Test example 1.

TABLE 3

| Compound No. to be tested | Amount of active ingredient (g/a) | Herbicidal effect | | |
|---|---|---|---|---|
| | | *Echinochloa crusgalli* | *Monochoria vaginalis* | *Scirpus juncoides* |
| 1 | 10 | 5 | 5 | 5 |
| 2 | 10 | 5 | 5 | 5 |
| 3 | 10 | 5 | 5 | 5 |
| 4 | 10 | 5 | 5 | 5 |
| 5 | 10 | 5 | 5 | 5 |
| 6 | 10 | 5 | 5 | 5 |
| 7 | 10 | 5 | 5 | 5 |
| 8 | 10 | 5 | 5 | 5 |
| 9 | 10 | 5 | 5 | 5 |
| 10 | 10 | 5 | 5 | 5 |
| 11 | 10 | 5 | 4 | 5 |
| 12 | 10 | 5 | 5 | 5 |
| 13 | 10 | 5 | 5 | 5 |
| 14 | 10 | 5 | 5 | 5 |
| 15 | 10 | 5 | 5 | 5 |
| 16 | 10 | 5 | 5 | 5 |
| 17 | 10 | 5 | 5 | 4 |
| 18 | 10 | 5 | 5 | 5 |
| 19 | 10 | 5 | 5 | 5 |
| 20 | 10 | 5 | 5 | 5 |
| 21 | 10 | 5 | 5 | 5 |
| 22 | 10 | 5 | 5 | 5 |
| 23 | 10 | 5 | 5 | 5 |
| 24 | 10 | 5 | 5 | 5 |
| 25 | 10 | 5 | 5 | 5 |
| 26 | 10 | 5 | 5 | 5 |
| 27 | 10 | 5 | 5 | 5 |
| 28 | 10 | 5 | 5 | 5 |
| 29 | 10 | 5 | 5 | 5 |
| 30 | 10 | 5 | 4 | 4 |
| 31 | 10 | 5 | 5 | 5 |
| 32 | 10 | 5 | 5 | 5 |
| 33 | 10 | 5 | 5 | 5 |
| 34 | 10 | 5 | 5 | 5 |
| 35 | 10 | 5 | 5 | 5 |
| 36 | 10 | 5 | 5 | 4 |
| 37 | 10 | 5 | 4 | 5 |
| 38 | 10 | 5 | 5 | 5 |
| 39 | 10 | 5 | 5 | 5 |
| 40 | 10 | 5 | 5 | 5 |
| 41 | 10 | 5 | 5 | 5 |
| 42 | 10 | 5 | 5 | 5 |
| 43 | 10 | 5 | 5 | 5 |
| 44 | 10 | 5 | 4 | 5 |
| 45 | 10 | 5 | 5 | 5 |
| 46 | 10 | 5 | 5 | 5 |
| 47 | 10 | 5 | 5 | 5 |
| 48 | 10 | 5 | 5 | 5 |
| 49 | 10 | 5 | 5 | 5 |
| 50 | 10 | 5 | 5 | 5 |
| 51 | 10 | 5 | 5 | 5 |
| 52 | 10 | 5 | 5 | 5 |
| 53 | 10 | 5 | 5 | 5 |
| 54 | 10 | 5 | 5 | 5 |
| 55 | 10 | 5 | 5 | 5 |
| 56 | 10 | 5 | 5 | 5 |
| 57 | 10 | 5 | 5 | 5 |
| 58 | 10 | 5 | 5 | 5 |
| 59 | 10 | 5 | 5 | 5 |
| Known compound A | 10 | 0 | 0 | 0 |

TABLE 4

| Compound No. to be tested | Amount of active ingredient (g/a) | Herbicidal effect | | |
|---|---|---|---|---|
| | | Digitaria sanguinalis | Echinochloa crusgalli | Setaria viridis |
| 1 | 10 | 5 | 5 | 5 |
| 5 | 10 | 5 | 5 | 4 |
| 6 | 10 | 5 | 5 | 5 |
| 8 | 10 | 5 | 5 | 5 |
| 10 | 10 | 5 | 5 | 5 |
| 11 | 10 | 5 | 5 | 5 |
| 12 | 10 | 5 | 5 | 5 |
| 13 | 10 | 5 | 5 | 5 |
| 14 | 10 | 5 | 5 | 5 |
| 15 | 10 | 5 | 5 | 5 |
| 17 | 10 | 5 | 5 | 5 |
| 18 | 10 | 5 | 5 | 5 |
| 20 | 10 | 5 | 5 | 5 |
| 21 | 10 | 5 | 5 | 5 |
| 22 | 10 | 5 | 5 | 4 |
| 24 | 10 | 5 | 5 | 5 |
| 27 | 10 | 5 | 4 | 5 |
| 31 | 10 | 5 | 5 | 5 |
| 32 | 10 | 5 | 5 | 5 |
| 33 | 10 | 5 | 5 | 5 |
| 34 | 10 | 5 | 5 | 4 |
| 35 | 10 | 5 | 5 | 5 |
| 36 | 10 | 5 | 5 | 5 |
| 37 | 10 | 5 | 5 | 5 |
| 43 | 10 | 5 | 4 | 5 |
| 45 | 10 | 5 | 5 | 5 |
| 46 | 10 | 5 | 5 | 5 |
| 47 | 10 | 5 | 5 | 5 |
| 48 | 10 | 5 | 5 | 5 |
| 50 | 10 | 5 | 5 | 5 |
| 51 | 10 | 5 | 5 | 5 |
| 52 | 10 | 5 | 5 | 5 |
| 53 | 10 | 5 | 5 | 5 |
| 55 | 10 | 5 | 5 | 5 |
| 56 | 10 | 5 | 5 | 5 |
| 58 | 10 | 5 | 5 | 5 |
| 59 | 10 | 5 | 5 | 5 |
| Known compound A | 10 | 0 | 0 | 0 |

What is claimed is:

1. An indan-1,3-dione derivative represented by the following formula (I):

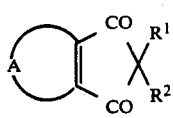

wherein $R^1$ represents a hydrogen atom or a lower alkyl group; $R^2$ represents a group represented by

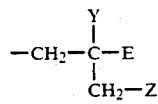

wherein E represents a phenyl group or a pyridyl group each of which may be substituted by 1 to 3 substituents selected from the group consisting of a halogen atom, a $C_1$-$C_4$ alkyl group, a $C_1$-$C_3$ haloalkyl group having 1 to 5 halogen atoms, a $C_1$-$C_2$ alkoxy group, a $C_1$-$C_2$ haloalkoxy group having 1 to 5 halogen atoms, a nitro group and a cyano group; Y represents a hydroxyl group; and Z represents an alkylsulfonyloxy group which may be substituted by a halogen atom or a phenyl group, or a phenylsulfonyloxy group which may be substituted by a substituent selected from the group consisting of halogen atoms, a $C_1$-$C_3$ alkyl group, a $C_1$-$C_3$ haloalkyl group having 1 to 5 halogen atoms, a $C_1$-$C_2$ alkoxy group, a $C_1$-$C_2$ haloalkoxy group having 1 to 5 halogen atoms, a tetramethylene group, a nitro group and a cyano group; and A represents a 1,3-butadienylene group which may be substituted by 1 to 4 substituents selected from the group consisting of a halogen atom, a $C_1$-$C_3$ alkyl group, a $C_1$-$C_3$ haloalkyl group having 1 to 5 halogen atoms, a $C_1$-$C_2$ alkoxy group, a $C_1$-$C_2$ haloalkoxy group having 1 to 4 halogen atoms, a nitro group and a cyano group; or a 1,3-azabutadienylene group which may be substituted by 1 to 3 substituents selected from the group consisting of a halogen atom, a $C_1$-$C_3$ alkyl group, a $C_1$-$C_3$ haloalkyl group having 1 to 5 halogen atoms, a $C_1$-$C_2$ alkoxy group, a $C_1$-$C_2$ haloalkoxy group having 1 to 4 halogen atoms, a nitro group and a cyano group.

2. The indan-1,3-dione derivative according to claim 1, wherein said lower alkyl group is a straight or branched $C_1$-$C_6$ alkyl group.

3. The indan-1,3-dione derivative according to claim 1, wherein said alkylsulfonyloxy group is a ($C_1$-$C_8$ alkyl)sulfonyloxy group which may be substituted by a halogen atom.

4. The indan-1,3-dione derivative according to claim 1, wherein said alkylsulfonyloxy group is a ($C_1$-$C_6$ alkyl)sulfonyloxy group which may be substituted by one or two halogen atoms.

5. The indan-1,3-dione derivative according to claim 1, wherein said phenylsulfonyloxy group is one which may be substituted by 1 to 3 substituents.

6. A herbicidal composition comprising an effective amount of the indan-1,3-dione derivative according to claim 1 and a herbicidally acceptable adjuvant.

7. A method for controlling gramineous weeds or cyperaceous weeds comprising applying a herbicidally effective amount of the indan-1,3-dione derivative according to claim 1 to said weeds.

* * * * *